(12) United States Patent
Tixier

(10) Patent No.: US 10,935,368 B2
(45) Date of Patent: Mar. 2, 2021

(54) SCANNING CALIPER AND BASIS WEIGHT SENSOR FOR SHEET PRODUCTS USING TERAHERTZ

(71) Applicant: Honeywell Limited, Mississauga (CA)

(72) Inventor: Sebastien Tixier, North Vancouver (CA)

(73) Assignee: Honeywell Limited, Mississauga (CA)

( * ) Notice: Subject to any disclaimer, the term of this patent is extended or adjusted under 35 U.S.C. 154(b) by 189 days.

(21) Appl. No.: 15/921,600

(22) Filed: Mar. 14, 2018

(65) Prior Publication Data
US 2019/0285527 A1 Sep. 19, 2019

(51) Int. Cl.
| | | |
|---|---|---|
| G01B 11/06 | (2006.01) | |
| G01N 9/36 | (2006.01) | |
| G01N 33/34 | (2006.01) | |
| G01N 9/24 | (2006.01) | |
| G01N 22/00 | (2006.01) | |
| G01B 11/02 | (2006.01) | |

(52) U.S. Cl.
CPC ............. *G01B 11/06* (2013.01); *G01B 11/02* (2013.01); *G01B 11/0691* (2013.01); *G01N 9/24* (2013.01); *G01N 9/36* (2013.01); *G01N 22/00* (2013.01); *G01N 33/346* (2013.01)

(58) Field of Classification Search
CPC ............ G01N 9/36; G01N 22/00; G01N 9/24; G01N 33/346; G01G 17/02; G01B 11/00; G01B 11/02; G01B 11/06; G01B 11/0691; G01B 7/14
See application file for complete search history.

(56) References Cited

U.S. PATENT DOCUMENTS

| | | |
|---|---|---|
| 4,160,204 A | 7/1979 | Holmgren et al. |
| 6,281,679 B1 | 8/2001 | King et al. |
| 6,967,726 B2 | 11/2005 | King et al. |
| 8,114,253 B2 | 2/2012 | Jez et al. |
| 8,314,391 B2 | 11/2012 | Haran et al. |
| 8,378,304 B2 | 2/2013 | Mousavi et al. |
| 8,527,212 B2 | 9/2013 | Hughes et al. |
| 8,660,682 B2 | 2/2014 | Hofman et al. |
| 8,760,669 B2 | 6/2014 | Heath et al. |
| 9,182,281 B1 | 11/2015 | Savard |
| 9,239,286 B2 | 1/2016 | Saeedkia |
| 9,441,961 B2 | 9/2016 | Haran et al. |
| 2015/0268030 A1* | 9/2015 | White ..................... H04J 14/02 250/353 |
| 2017/0023469 A1* | 1/2017 | Zimdars ............. G01N 21/3581 |

\* cited by examiner

*Primary Examiner* — Amy He
(74) *Attorney, Agent, or Firm* — Charles H Jew

(57) ABSTRACT

Time-of-flight measurements calculate the absolute caliper of a moving film independent of the film's index of refraction. A reflective fiber coupled terahertz gauge is mounted co-axially with a temperature stabilized Z-sensor positioned within a scanner head. The terahertz gauge monitors four reflections: (1) the reflection from a sensor window, (2, 3) the reflections from the top and bottom surfaces of the sheet product being measured, and (4) the reflection from a reflector that is placed behind the sheet. The Z-sensor monitors the distance between the reflector and the sensor window. The terahertz reflection delays together with the Z distance measurements allow extraction of the caliper. Since the time delay due to the sheet is a function of thickness and index of refraction, the basis weight of the sheet can be determined by using a calibration of the sensor relating basis weight of the product to time delay.

20 Claims, 4 Drawing Sheets

SCANNING CALIPER AND BASIS WEIGHT SENSOR FOR SHEET PRODUCTS USING TERAHERTZ

FIELD OF THE INVENTION

The present invention relates generally to techniques for non-contacting caliper and basis weight measurements of a moving sheet, web or film such as polymer and paper using terahertz time-of-flight techniques.

BACKGROUND OF THE INVENTION

Infrared and nuclear sensors are used for on-line measurements in the flat sheet industries. Infrared sensors are limited in application due to the weak penetration of light in heavy or opaque products. Infrared sensors also suffer from requiring a complex calibration procedure especially when measuring multi-ply or multi-layer products. Nuclear sensors have the advantage of being able to measure basis weight directly with little sensitivity to the exact product composition but these sensors cannot measure individual layers in multi-ply applications. Moreover, nuclear sensors pose serious safety concerns and are expensive to maintain. Terahertz sensors can address these shortcomings but one problem with current terahertz devices is that the index of refraction of the product must be known in order to produce an absolute caliper. Manufacturers often do not know their product's index of refraction which changes with composition and material density.

SUMMARY OF THE INVENTION

The present invention is based in part on the recognition that time-of-flight measurements can be employed to calculate the absolute caliper of a moving film without having to know the film's index of refraction. The inventive scanning terahertz sensor can achieve robust, accurate thickness measurements independent of product density.

In one aspect, the invention is directed to a non-contact method of measuring at least one property of a moving film, which has a first exterior (top) side, a second exterior (bottom) side, a first interior side and a second interior side, and which travels in a machine direction, that includes:

(a) providing a sensor device that includes (i) a first scanner head having a layer of transparent material, which is transparent to terahertz and defines a first (upper) sheet guide surface, (ii) a reflective member having a reflective surface, which reflects terahertz radiation, wherein the reflective surface defines a second (lower) sheet guide surface, and wherein the first (upper) sheet guide surface and the second (lower) sheet guide surface define a measurement gap through which the moving film travels in the machine direction;

(b) measuring the distance of the measurement gap;

(c) providing a source of terahertz radiation that generates terahertz radiation, which is positioned in the first scanner head, and directing the terahertz radiation through the first layer of material and toward the first exterior of the moving film which travels through the measurement gap such that the first sheet guide faces the first exterior side of the moving film and the second sheet guide faces the second exterior side of the moving film;

(d) providing a detector, which is positioned in the first scanner head, to receive (i) first terahertz radiation that is reflected from the interior surface of the layer of transparent material, (ii) second terahertz radiation that is reflected from the first exterior (top) side of the film, (iii) third terahertz radiation that is reflected from the second interior surface of the film, and (iv) fourth terahertz radiation that is reflected from the reflective surface, wherein the detector is configured to output measurement data corresponding to detection of the first, second, third and fourth terahertz radiation; and (e) calculating (i) the caliper of the moving film independent of the refractive index of the film based on arrival times of the first, second, third and fourth terahertz radiation and/or (ii) the basis weight of the moving film based on arrival times of the first, second, third and fourth terahertz radiation.

In another aspect, the invention is directed to a scanning sensor for measuring at least one property of a continuous sheet, which has a first exterior (top) side, a second exterior (bottom) side, a first interior side and a second interior side, and which travels in a machine direction, that includes:

a first scanner head disposed adjacent to the first exterior side of the sheet and comprises a layer of transparent material, that faces the first exterior side of the sheet, and which is transparent to terahertz radiation, and that defines a first (upper) sheet guide surface;

a reflective member having reflective surface, which is reflective of terahertz radiation, and that is facing the second exterior side of the sheet, wherein the reflective surface defines a second (lower) sheet guide surface, and wherein the first (upper) sheet guide surface and the second sheet guide surface define a measurement gap through which the continuous sheet travels in the machine direction;

a source of terahertz radiation, which is positioned in the first scanner head, and which is configured to generates terahertz radiation that is transmitted through the first layer of material and toward the first exterior side of the continuous sheet;

means for measuring the distance of the measurement gap;

a detector positioned in the first scanner head which is configured to receive (i) first terahertz radiation that is reflected from an interior surface of the layer of transparent material, (ii) second terahertz radiation that is reflected from the first exterior (top) side of the sheet, (iii) third terahertz radiation that is reflected from the second interior surface of the sheet, and (iv) fourth terahertz radiation that is reflected from the reflective surface, wherein the detector is configured to output measurement data corresponding to detection of the first, second, third and fourth terahertz radiation; and a processor in communication with the source of terahertz radiation and to the detector and which is configured to determine (i) the caliper of the sheet independent of the refractive index of the sheet based on arrival times of the first, second, third and fourth terahertz radiation and/or (ii) the basis weight of the sheet based on arrival times of the first, second, third and fourth terahertz radiation.

Terahertz radiation, also known as terahertz waves, terahertz radiation or T-rays, generally refers to the region of the electromagnetic spectrum between 300 gigahertz ($3 \times 10^{11}$ Hz) and 3 terahertz ($3 \times 10^{12}$ Hz), corresponding to the sub millimeter wavelength range between 1 millimeter (high-frequency edge of the microwave band) and 100 micrometers (long-wavelength edge of far-infrared radiation). For measuring the thickness and basis weight of paper and plastics, the source of terahertz radiation generates pulses of terahertz radiation having a frequency in the range of 300 GHz to greater than 4 THz. A narrow pulse of radiation (in time) generates a wide frequency bandwidth. That is, a very narrow sharp pulse has a very wide frequency spectrum and vice versa. It is preferred that the terahertz sensors employ a wide frequency bandwidth.

In a preferred embodiment, the terahertz scanning sensor includes a reflective fiber coupled terahertz gauge that is mounted co-axially with a temperature stabilized eddy-current Z-sensor that is positioned in a scanner head. The Z-coil's temperature is controlled with a thermoelectric cooler. In addition, it is particularly preferred that the ambient temperature within the enclosure of the scanner head is controlled with a heat exchanger. Regulating the temperatures of both the Z-sensor and enclosure ensures sub-micron accuracy and stability of the caliper measurements. The terahertz gauge monitors four reflections: (1) the reflection from a sensor window, (2, 3) the reflections from the top and bottom surfaces of the sheet product being measured, and (4) the reflection from a reflector that is placed behind the sheet. In addition, the Z-sensor continuously monitors the separation between the reflector and the sensor window as the scanning head moves across the sheet. Knowledge of the terahertz reflection delays together with the distance between the sensor window and reflector allows extraction of caliper of the product independently of its index of refraction or density. Since the time delay due to the sheet is a function of its thickness and index of refraction, the basis weight of the sheet can be determined by developing a calibration formula or library relating basis weight of the product to time delay.

While the non-contact sensor will be illustrated in calculating the caliper and basis weight of paper, it is understood that the sensor can measure physical properties of a variety of flat materials in the form of film, web or sheet including, for example, coated materials, plastics, fabrics, and the like. The terahertz sensor is particularly suited for measuring the caliper of paper having a thickness from 5 microns to at least 3 mm and for plastic having a thickness from 5 microns to 3 cm. The higher thickness limits for plastic is due to the lower interaction strength of terahertz radiation to most plastics.

DETAILED DESCRIPTION OF PREFERRED EMBODIMENTS

Figure 1A:
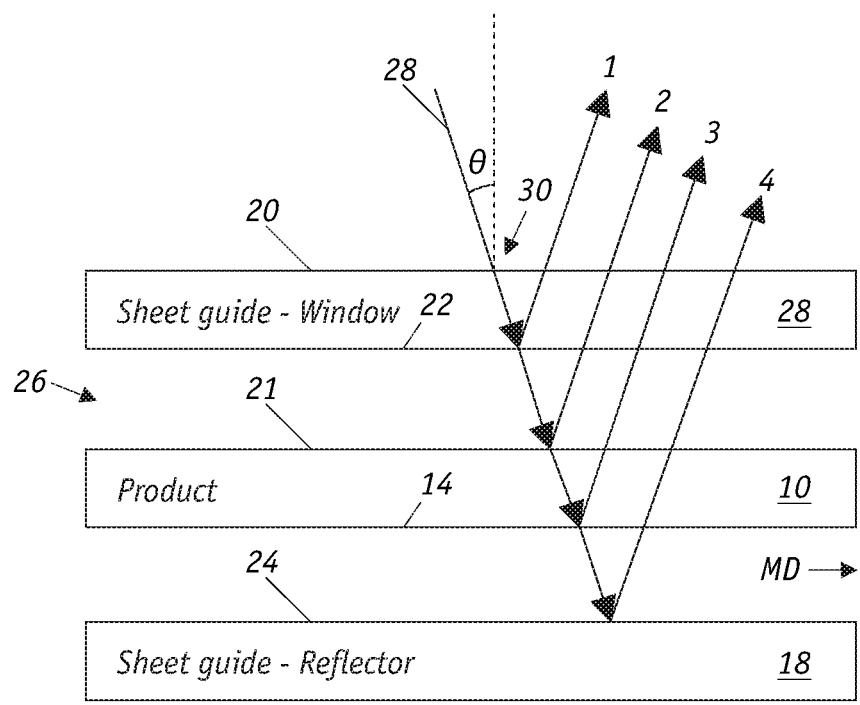
FIG. 1A shows the reflections of an incident terahertz radiation beam as the beam is transmitted through a sheet or film product that is situated in a measurement gap that is between upper and lower sheet guides.
Figure 1B:
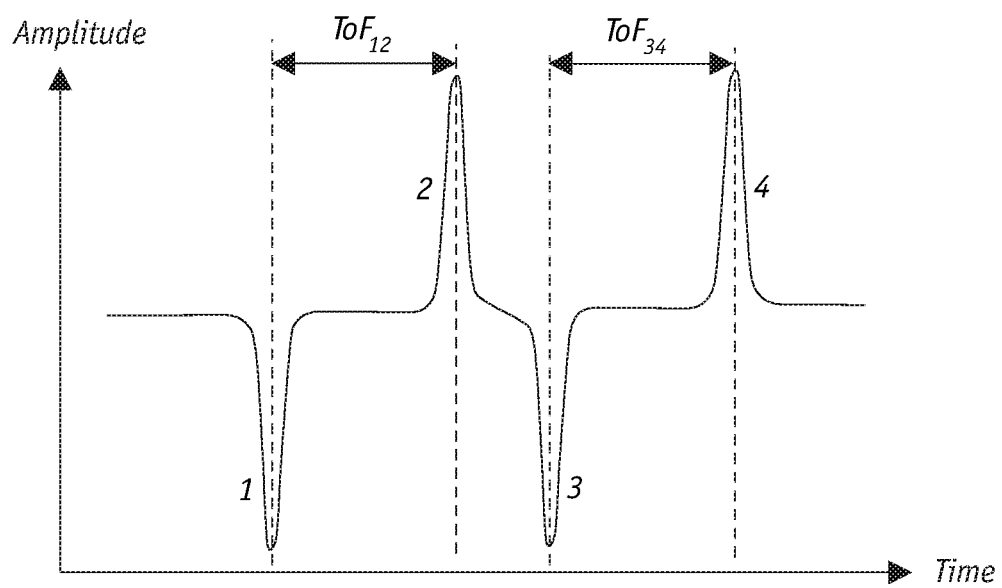
FIG. 1B is a graph of amplitude vs. time from detector radiation intensity measurements corresponding to reflected radiation.

FIGS. 1A and 1B illustrate a technique for measuring the absolute caliper of a sheet or film product 10, that has an upper exterior surface 21 and interior surface 14, and which is traveling in the machine direction (MD) through a measurement gap or channel 26 that is formed between upper sheet guide 28 and lower sheet guide 18. The upper sheet guide or window 28 is preferably made of silicon, sapphire, plastic or other terahertz grade materials that are transparent to terahertz radiation and is typically from 500 microns to 2-3 mm thick. Window 28 has an upper exterior surface 20 and interior surface 22. The lower sheet guide or reflector 18 has an upper surface 24 that is reflective of terahertz radiation. The upper surface 24 can be a metallic mirror or reflector that is made of gold, silver, aluminum coated glass or polished aluminum.

A beam of incident terahertz radiation 28 is directed toward window 28 at an incident angle θ, wherein the beam of radiation reaches a fixed position 30 on the exposed surface 20. The angle of incidence is typically from 0 to 60 degrees with respect to the sheet surface normal. Radiation beams 1, 2, 3, and 4 are reflected from surfaces 22, 21, 14, and 24, respectively. The reflected radiation is detected by a terahertz detector.

FIG. 1B shows the amplitude of the detected radiation vs. time. $ToF_{12}$ and $ToF_{34}$ are the time-of-flight differences due to the time light takes to travel through the portion of measuring gap (also referred as "time delays") that is above product 10 and through the portion that is below the product 10. The absolute caliper of the product 10 can be calculated by subtracting $ToF_{12}$ and $ToF_{34}$ from ToF empty, which is the time-of-flight when there is no product in the gap, and multiplying the difference by c, the speed of light in air within the measurement gap. The refractive index of air for terahertz radiation is about 1.0003 which is very close to that in vacuum. In this fashion, in order to calculate absolute caliper of a product, it is not necessary to measure the time that the light takes to travel through the product. In additional to or instead of measuring ToF empty with the terahertz gauge, which is referred to as an "off-sheet" measurement, a Z-sensor can be employed to continuously determine the measurement gap distance between surfaces 22 and 24 as the product is moving through the gap. The gap distance can vary due to temperature variations and mechanical defects of the scanning system in which the on-line scanning terahertz sensor is incorporated such as beam sag, beam mis-alignment, and scanner head carriage wheel wear.

Figure 2:
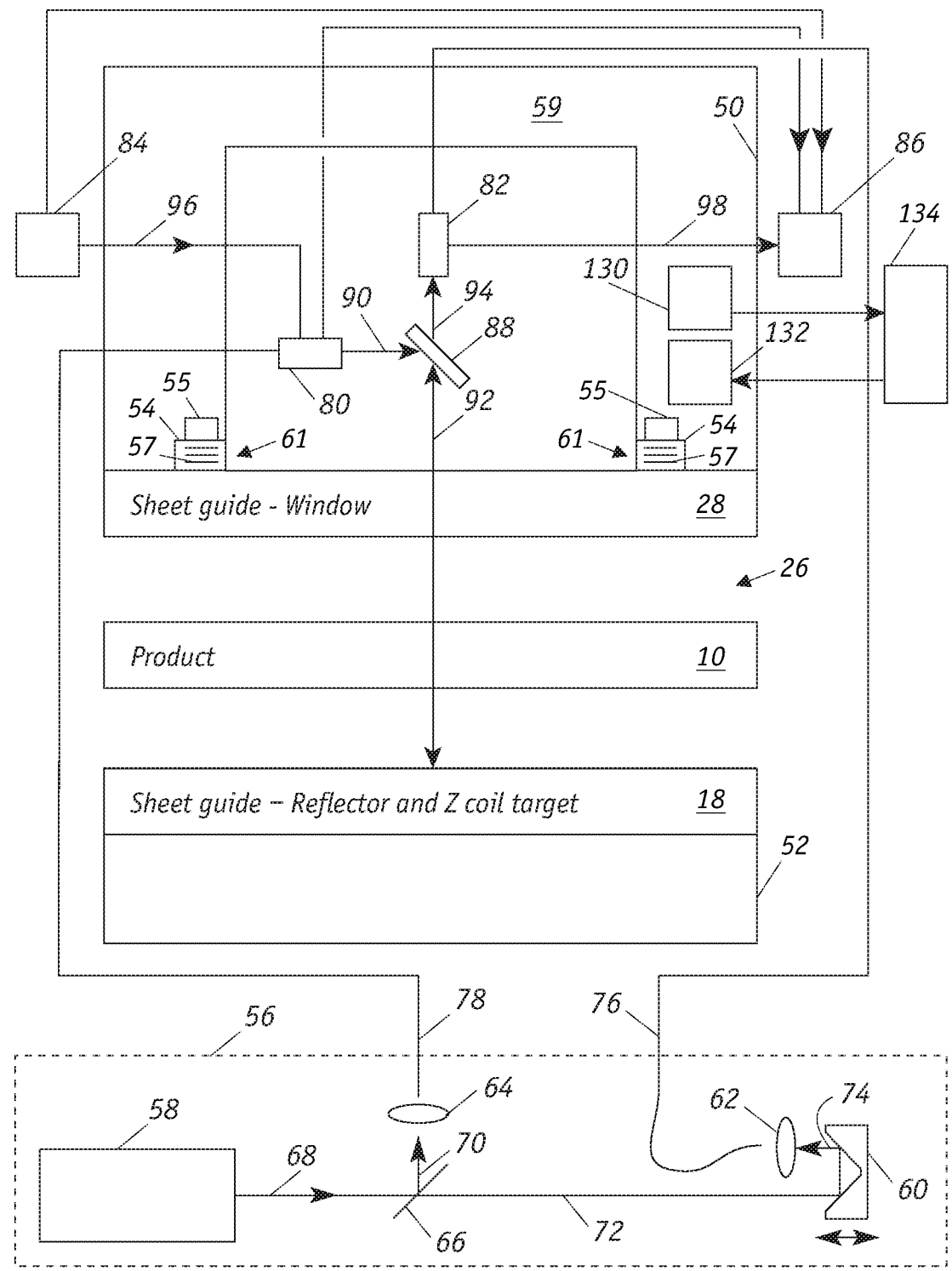
FIG. 2 shows an on-line scanning terahertz sensor system for absolute caliper and basis weight measurements.

FIG. 2 illustrates a scanning sensor with a terahertz time-domain spectrometer for monitoring at least one property of the moving sheet or web of material 10. The basic components of the spectrometer include: pulsed laser source 58, beam splitter 66, terahertz transmitter 80, modulated power source 84, terahertz receiver or detector 82, spectroscopic analyzer 86, and optical delay device 60, each of which consists of a conventional device. Pulsed laser source 58, such as a femto-second pulse laser, generates pump signals 68 that are directed toward beam splitter 66 which splits the light pulses of pump signals 68 to yield excitation light 70 and detector gating light 72. The terahertz transmitter and detector can comprise a photoconductive antenna that consists of a highly reflective direct semiconductor thin film such as GaAs with two electric contact pads. In the case of a THz transmitter a voltage is connected to the contacts. For a detector, an amplifier is connected to the contacts; in this configuration, the terahertz electric field is measured, which means that the signal across the GaAs detector can be positive or negative, depending on the orientation of the electric field.

Excitation light 70 is focused by objective lens 64 and launched into and transmitted through delivery fiber optic cable or optical fiber 78. Excitation light 70 illuminates transmitter 80 to generate terahertz radiation or T-rays 91 which are directed by beam splitter 88 into moving sheet 10. Modulated power source 84 supplies an electrical input 96 into terahertz transmitter 80. Radiation 94 that is reflected from the upper sheet guide or window 28, moving sheet 10 and lower sheet guide or reflector 18 pass through the beam splitter 88 and is captured by detector 82.

Detector gating light 72 is directed to optical delay device 60 which serves to set or modify the difference between the timing of the detector gate light 72 and the timing of the excitation light 70. Optical delay device 60 includes a movable retro-reflector. Changing the position of movable retro-reflector changes the length of the optical path of detector gating light 72, thereby changing and setting the difference between excitation light irradiation timing (T-ray generating timing) and the detector gating light irradiation timing (T-ray detecting timing). Objective lens 62 directs detector gating light 74 from optical delay device 80 and launches the light into delivery fiber optic cable or optical fiber 76 and into receiver or detector 82. The laser pulses that exit from the end of fiber optical cable 76 are used to effectively switch on the terahertz receiver in a synchronous detection scheme. When the arrival times of these synchronizing pulses to the terahertz receiver are varied, the terahertz pulses can be traced out. The output 98 from receiver 82 is an electrical signal that is typically amplified and digitized and then read into a computer for analysis or alternatively the electrical signal can be analyzed in a digital signal processor. The electrical signal can be amplified with a transimpedance amplifier and then fed into a lockin amplifier. If lockin detection is employed, a modulated bias voltage is typically applied to power source 84. The lockin detector is then synchronized with this bias modulation. Instead of modulating the bias voltage, the terahertz beam can be modulated with a chopper.

Detector 82 generates detection signals 98 which are transmitted to spectroscopic analyzer 86, which is typically a computer. The electrical signals generated by the detector containing output measurement data are analyzed in the computer in the temporal or frequency domain. For instance, this analysis can also be done in a Field-Programmable Gate Array or a Digital Signal Processor. While optical delay device 60 is positioned in the optical path of detector light 72, an optical delay device could be positioned in the optical path of excitation light 74 instead. Preferably, laser source 58, beam splitter 66, optical delay device 60, and objective lens 64 and 62 are housed in compartment 56. The terahertz transmitter 80 and receiver 82 are located within enclosure 59 of upper sensor head 50.

Enclosure 59 also houses a displacement or distance measurement apparatus that measures the vertical distance (z) between the planar operative surfaces of lower and upper sheet guides 18, 28. Suitable apparatuses, for example, include temperature stabilized magnetic, inductive, and eddy-current sensors. These sensors require a metallic target. An eddy current sensor, which is an inductive-type sensor, is preferred. As illustrated, the eddy current sensor 61 includes a high thermally conductive aluminum nitride housing 54 that contains an RF or Z-coil 57, which is made of copper or other non-ferrous material. The RF or Z-coil 57 is concentric with terahertz beam 92. The temperature of the Z-coil 57 is controlled with a Peltier cooler 55 which is in thermal contact with the aluminum nitride housing 54. The air ambient temperature within enclosure 59 of scanner head 50 can be regulated with controller 134, which actuates heat exchanger 132 in response to signals from temperature sensor 130. The heat exchanger typically includes circulating coolant and a fan. Employing both the Peltier cooler for Z-coil temperature control and the heat exchanger for scanner head temperature control affords robust sub-micron accuracy and stability for continuous caliper measurements.

The upper exterior surface of lower sheet guide 18 thus serves as the reflector surface for the terahertz radiation and as the Z-coil reference surface or target. In this arrangement, the Z-sensor 54 measures the distance from the coil to the reference surface, thus, it is necessary to subtract the thickness of upper sheet guide 28 to calculate the gap distance. The temperature of the Z-coil in the upper scanner head 50 Lower scanner head 52 serves as a support member for lower sheet guide 18.

The preferred angle of incidence of the terahertz radiation is normal to the upper surface of the window sheet guide, that is, incident angle $\theta$ (FIG. 1A) is zero. In this configuration, the sensor is more immune to changes in the standoff distance, which is the distance from sensor to the moving sheet. Even when the terahertz radiation pulses entered the sheet product at a normal angle, there is enough index of refraction (or dielectric constant) contrast to get a reflection. If the window sheet guide is too thin, there can be a potential cancellation effect and/or distortion effect because the reflection from the air-window and the reflection from the window-air interface have opposite signs. However, these reflections are separated enough in time when using 2-3 mm thick windows.

Figure 3:
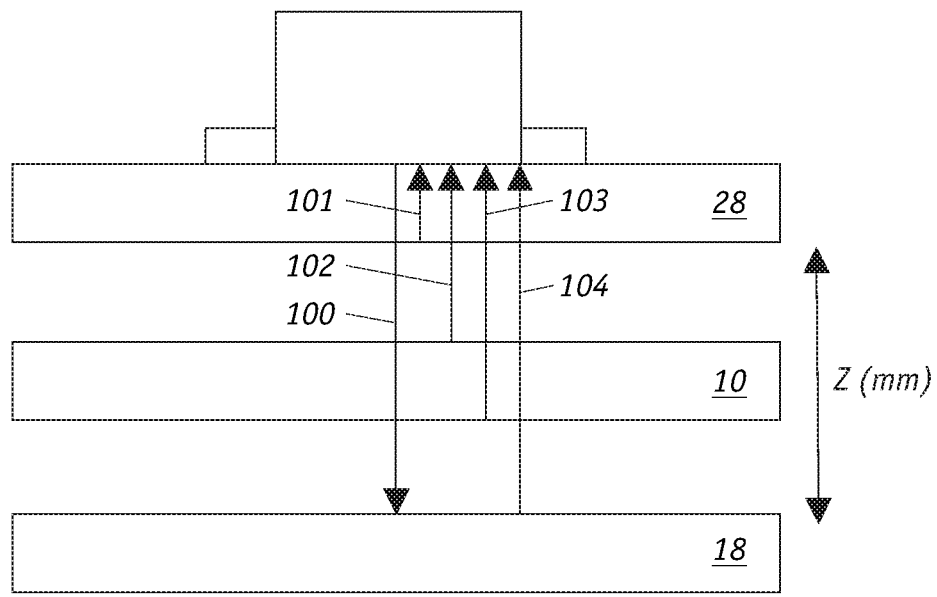
FIG. 3 shows the reflections of an incident terahertz radiation beam during operation of the terahertz sensor.

FIG. 3 depicts the reflections of the terahertz radiation during operation of the sensor wherein the beam 100 of terahertz radiation is directed at a normal angle of incidence. The reflected rays separated for ease of illustration, it is understood that the reflected rays travel along the same beam path as that of beam 100. After pulses of terahertz radiation penetrate through window 28 and product 10, terahertz radiation is reflected from the interior surface of window 28, exterior and interior surfaces of the product 10, and exterior surface of reflector surface 18. These reflections are designated 101, 102, 103, and 104, respectively. Terahertz can be used to analyze multilayer products. Reflections from all the product interfaces can be detected and measured. The technique requires a difference in index of refraction (or dielectric properties) between the adjacent layers and each of the adjacent layers is at least 10-20 microns thick.

Measurements from the terahertz scanner can also be used to calculate the basis weight (BW), which for paper, is expressed in grams per square meter (gsm). The time delay shown in FIG. 3 due to sheet 10 is a function of its thickness and index of refraction. The gauge is calibrated to output BW (in gsm) from the time delay typically in picosecond (ps) using standards of known composition, index of refraction, basis weight and thickness. The calibration curve or relationship is a linear one: BW=BWslope×delay+BWint where BWslope and BWint are calibration constants. The calibration constants will be sensitive to the exact sample composition. A high order polynomial fit for a large basis weight range may be required as a linear fit may not be adequate. A library of basis weight to time delay data can be established and used.

Figure 4:
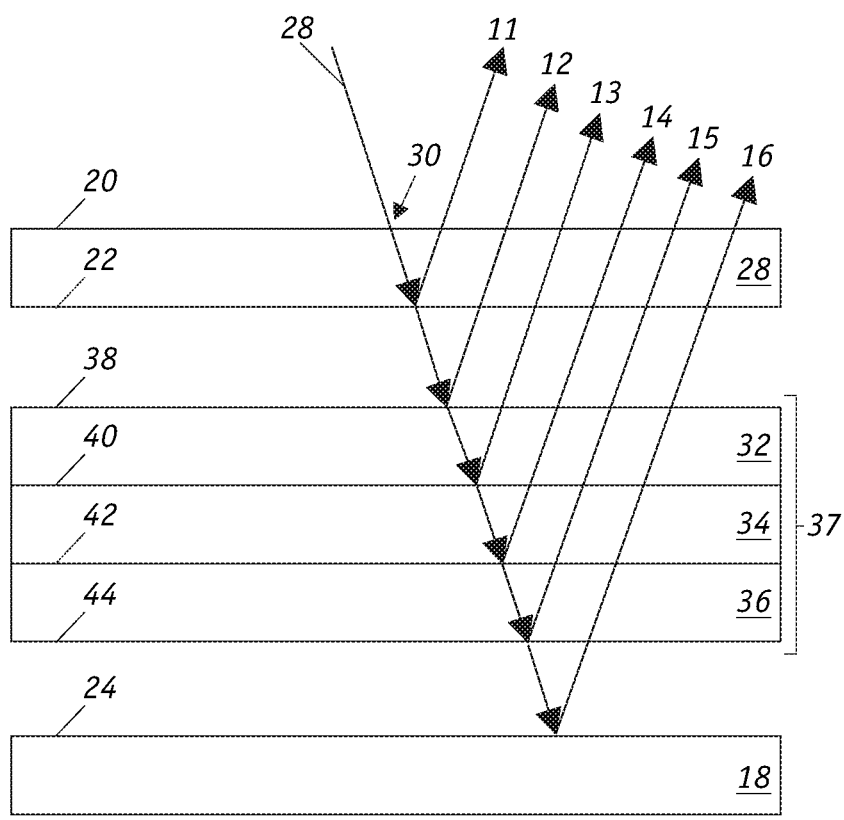
FIG. 4 shows the reflections of an incident terahertz radiation beam as the beam is transmitted through a multilayer film product that is situated in a measurement gap that is between upper and lower sheet guides.

FIG. 4 depicts the reflections of terahertz radiation when analyzing a multilayer film that is traveling through a measurement gap defined by upper sheet guide 28 and lower sheet guide 18. Upper sheet guide or window an upper exterior surface 20 and interior surface 22 and the lower sheet guide or reflector 18 has an upper surface 24. The planar product 37 is multilayer film consisting of three layers 32, 32, and 35. The film has an upper surface 38 and lower interior surface 44. There is an interface 40 between layers 32 and 34 and an interface 42 between layers 34 and 36.

A beam of incident terahertz radiation 28 is directed toward window 28 at an incident angle θ, wherein the beam of radiation reaches a fixed position 30 on the exposed surface 20. Radiation beams 11, 12, 13, 14, 15, and 16 are reflected from surfaces 22, 38, interfaces 40, and 42, and surfaces 44 and 24, respectively. The reflected radiation is detected by a terahertz detector (not shown) and the amplitude of the detected radiation vs. time can be recorded. $ToF_{12}$ and $ToF_{34}$ are the time-of-flight differences due to the time light takes to travel through the portion of measuring gap that is above product 37 and through the portion that is below the product. The absolute caliper of the product 37 can be measured by subtracting ToF empty, which is the time-of-flight when there is no product in the gap, by $ToF_{12}$ and $ToF_{34}$. In this fashion, it is not necessary to measure the time that the light takes to travel through the product. Instead of measuring ToF empty, Z-sensor can be employed to continuously measure the measurement gap distance between surfaces 22 and 24. The reflection beams 12, 13, 14, 15 and 16 are immediate reflections that correspond to the number of layers in the multilayer film. The individual layer thickness of the product can be calculated but this would not be an absolute measurement, which would require knowing the index of refraction to extract physical thickness. The index of refraction of a film can be independently measured with a refractometer. If the film is made of a known composition, its index of refraction is usually available from published sources.

Figure 5:
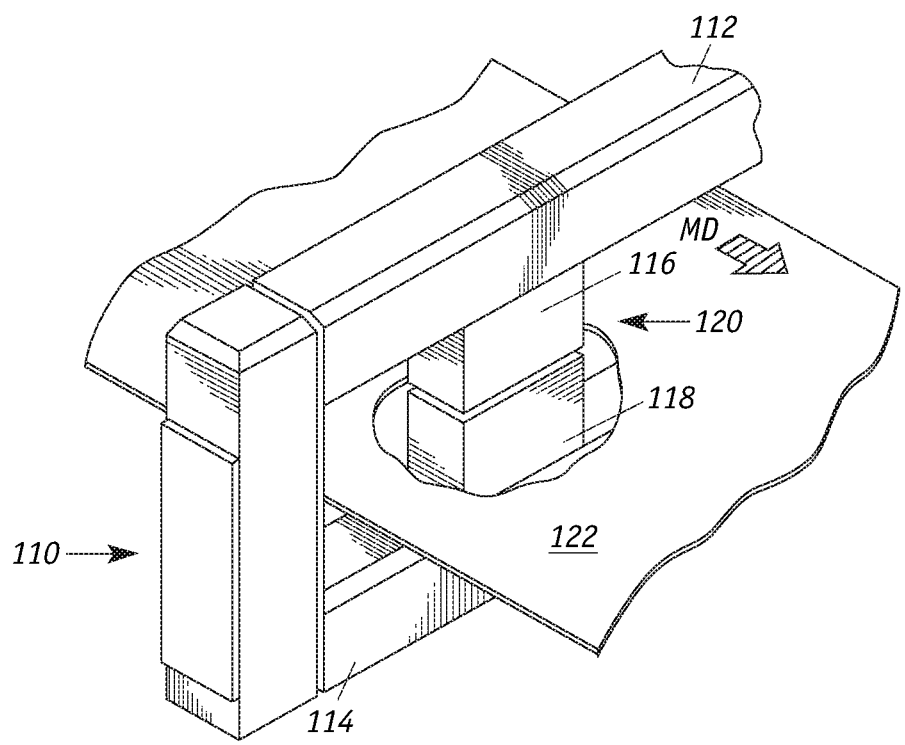
FIG. 5 shows an on-line scanning system with synchronized dual scanner heads.

The FIG. 5 illustrates an implementation of the sensor that is shown in FIG. 2 used during production of paper or plastic to provide on-line thickness measurements. The scanning system 110 includes two transverse beams 112 and 114 on which are mounted upper and lower scanning heads 116 and 118, respectively. The planar operative faces of the lower and upper scanner heads define a measurement gap or window that accommodates sheet 122. The radiation source and detector are housed in upper head scanner 116. The lower scanner head 56 may include a sheet stabilization system such as an air-bearing stabilizer (not shown) to maintain the sheet on a consistent plane as it passes through the measurement window. The movement of the dual scanner heads is synchronized with respect to speed and direction so that they are aligned with each other. The canner heads move repeatedly back and forth in the CD across the width of the moving sheet, which moves in the MD, so that the characteristics of the entire sheet may be measured.

The foregoing has described the principles, preferred embodiment and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of present invention as defined by the following claims.

What is claimed is:

1. A scanning sensor for measuring at least one property of a continuous sheet that comprises paper having a thickness from 5 microns to 3 mm, which has a first exterior side, a second exterior side, a first interior side and a second interior side, and which travels in a machine direction, that comprises:

a first scanner head disposed adjacent to the first exterior side of the sheet and comprises a layer of transparent material, that faces the first exterior side of the sheet, and which is transparent to terahertz radiation, and that defines a first sheet guide surface and wherein the layer of transparent material has a first operative surface that comprises silicon, sapphire, quartz, or plastic which has a thickness of 500 microns to 3 mm;

a reflective member having a reflective surface, which is reflective of terahertz radiation, and that is facing the second exterior side of the sheet, wherein the reflective surface defines a second sheet guide surface, and wherein the first sheet guide surface and the second sheet guide surface define a measurement gap through which the continuous sheet travels in the machine direction;

a source of terahertz radiation, which is positioned in the first scanner head, and which is configured to generates terahertz radiation that is transmitted through the first layer of material and toward the first exterior side of the continuous sheet;

a temperature stabilized Z-sensor that is configured to measure the distance of the measurement gap wherein the Z-sensor's temperature is controlled by a cooler;

a detector positioned in the first scanner head which is configured to receive (i) first terahertz radiation that is reflected from an interior surface of the layer of transparent material, (ii) second terahertz radiation that is reflected from the first exterior (top) side of the sheet, (iii) third terahertz radiation that is reflected from the second interior surface of the sheet, and (iv) fourth terahertz radiation that is reflected from the reflective surface, wherein the detector is configured to output measurement data corresponding to detection of the first, second, third and fourth terahertz radiation; and a processor in communication with the source of terahertz radiation and to the detector and which is configured to determine (i) the caliper of the sheet independent of the refractive index of the sheet based on arrival times of the first, second, third and fourth terahertz radiation and/or (ii) the basis weight of the sheet based on arrival times of the first, second, third and fourth terahertz radiation.

2. The scanning sensor of claim 1 wherein the source of terahertz radiation generates terahertz radiation having a frequency in the range of 300 GHz to or greater than 4 THz.

3. The scanning sensor of claim 1 wherein the source of terahertz radiation generates pulses of terahertz radiation.

4. The scanning sensor of claim 1 wherein the reflective member includes a metallic mirror or reflector that is selected from gold, silver, polished aluminum or aluminum coated glass.

5. The scanning sensor of claim 1 further comprising a second scanner head disposed adjacent to the second exterior side of the sheet wherein the reflective member is secured to the second scanner head.

6. The scanning sensor of claim 1 wherein the Z-sensor is a magnetic, inductive, or eddy-current sensor.

7. The scanning sensor of claim 6 wherein the source of terahertz radiation generates a terahertz radiation beam and wherein the magnetic, inductive, or eddy-current sensor is concentric to the terahertz radiation beam.

8. The scanning sensor of claim 1 wherein the first scanner head includes an enclosure housing the Z-sensor and the first scanner head comprises means for regulating ambient temperature within the enclosure.

9. A non-contact method of measuring at least one property of a moving film that comprises paper having a thickness from 5 microns to 3 mm, which has a first exterior side, a second exterior side, a first interior side and a second interior side, and which travels in a machine direction, that comprises:
(a) providing a sensor device that includes (i) a first scanner head having a layer of transparent material, which is transparent to terahertz and defines a first sheet guide, and wherein the layer of transparent material has a first operative surface that comprises silicon, sapphire, quartz, or plastic which has a thickness of 500 microns to 3 mm (ii) a reflective member having a reflective surface, which is reflects terahertz radiation, wherein the reflective surface defines a second sheet guide surface, and wherein the first sheet guide surface and the second sheet guide surface define a measurement gap through which the moving film travels in the machine direction;
(b) measuring the distance of the measurement gap with a temperature stabilized Z-sensor wherein the Z-sensor's temperature is controlled by a cooler;
(c) providing a source of terahertz radiation that generates terahertz radiation, which is positioned in the first scanner head, and directing the terahertz radiation through the first layer of material and toward the first exterior of the moving film which travels through the measurement gap such that the first sheet guide faces the first exterior side of the moving film and the second sheet guide faces the second exterior side of the moving film;
(d) proving a detector, which is positioned in the first scanner head, to receive (i) first terahertz radiation that is reflected from the interior surface of the layer of transparent material, (ii) second terahertz radiation that is reflected from the first exterior (top) side of the film, (iii) third terahertz radiation that is reflected from the second interior surface of the film, and (iv) fourth terahertz radiation that is reflected from the reflective surface, wherein the detector is configured to output measurement data corresponding to detection of the first, second, third and fourth terahertz radiation; and
(e) calculating (i) the caliper of the moving film independent of the refractive index of the film based on arrival times of the first, second, third and fourth terahertz radiation and/or (ii) the basis weight of the moving the film based on arrival times of the first, second, third and fourth terahertz radiation.

10. The method of claim 9 wherein the moving film comprises a multilayered structure having two or more layers with corresponding one or more interfaces between adjacent layers and in step (d) the detector receives terahertz radiation that is reflected from the interface between each set of adjacent layers and step (e) comprises calculating (i) the caliper of one more layers of the moving film independent of the refractive indexes of individual layers of the film based on arrival times of the first, second, third and fourth terahertz radiation and/or (ii) the basis weight of one or more layers of the moving the film based on arrival times of the first, second, third and fourth terahertz radiation.

11. The method of claim 9 wherein step (b) comprises taking time-of-flight measurements of terahertz radiation traveling between the measurement gap.

12. The method of claim 9 wherein step (b) comprises using a magnetic, inductive, or eddy-current sensor.

13. The method of claim 12 wherein the source of terahertz radiation generates a terahertz radiation beam and wherein the magnetic, inductive, or eddy-current sensor is concentric to the terahertz radiation beam.

14. The method of claim 9 wherein the source of terahertz radiation generates terahertz radiation having a frequency in the range of 300 GHz to or greater than 4 THz.

15. The method of claim 9 wherein the source of terahertz radiation generates pulses of terahertz radiation.

16. The method of claim 9 wherein the first scanner head includes an enclosure housing the Z-sensor and further comprising regulating ambient temperature within the enclosure.

17. A scanning sensor for measuring at least one property of a continuous sheet that comprises plastic having a thickness from 5 microns to 3 cm, which has a first exterior side, a second exterior side, a first interior side and a second interior side, and which travels in a machine direction, that comprises:
a first scanner head disposed adjacent to the first exterior side of the sheet and comprises a layer of transparent material, that faces the first exterior side of the sheet, and which is transparent to terahertz radiation, and that defines a first sheet guide surface wherein the layer of transparent material has a first operative surface that comprises silicon, sapphire, quartz, or plastic which has a thickness of 500 microns to 3 mm;
a reflective member having a reflective surface, which is reflective of terahertz radiation, and that is facing the second exterior side of the sheet, wherein the reflective surface defines a second sheet guide surface, and wherein the first sheet guide surface and the second sheet guide surface define a measurement gap through which the continuous sheet travels in the machine direction;
a source of terahertz radiation, which is positioned in the first scanner head, and which is configured to generates terahertz radiation that is transmitted through the first layer of material and toward the first exterior side of the continuous sheet;
a temperature stabilized Z-sensor that is configured to measure the distance of the measurement gap wherein the Z-sensor's temperature is controlled by a cooler;
a detector positioned in the first scanner head which is configured to receive (i) first terahertz radiation that is reflected from an interior surface of the layer of transparent material, (ii) second terahertz radiation that is reflected from the first exterior (top) side of the sheet, (iii) third terahertz radiation that is reflected from the second interior surface of the sheet, and (iv) fourth terahertz radiation that is reflected from the reflective surface, wherein the detector is configured to output measurement data corresponding to detection of the first, second, third and fourth terahertz radiation; and
a processor in communication with the source of terahertz radiation and to the detector and which is configured to determine (i) the caliper of the sheet independent of the refractive index of the sheet based on arrival times of the first, second, third and fourth terahertz radiation and/or (ii) the basis weight of the sheet based on arrival times of the first, second, third and fourth terahertz radiation.

18. The scanning sensor of claim 17 wherein the source of terahertz radiation generates terahertz radiation having a frequency in the range of 300 GHz to or greater than 4 THz.

19. A non-contact method of measuring at least one property of a moving film that comprises plastic having a thickness from 5 microns to 3 cm, which has a first exterior side, a second exterior side, a first interior side and a second interior side, and which travels in a machine direction, that comprises:

(a) providing a sensor device that includes (i) a first scanner head having a layer of transparent material, which is transparent to terahertz and defines a first sheet guide, and wherein the layer of transparent material has a first operative surface that comprises silicon, sapphire, quartz, or plastic which has a thickness of 500 microns to 3 mm (ii) a reflective member having a reflective surface, which is reflects terahertz radiation, wherein the reflective surface defines a second sheet guide surface, and wherein the first sheet guide surface and the second sheet guide surface define a measurement gap through which the moving film travels in the machine direction;

(b) measuring the distance of the measurement gap with a temperature stabilized Z-sensor wherein the Z-sensor's temperature is controlled by a cooler;

(c) providing a source of terahertz radiation that generates terahertz radiation, which is positioned in the first scanner head, and directing the terahertz radiation through the first layer of material and toward the first exterior of the moving film which travels through the measurement gap such that the first sheet guide faces the first exterior side of the moving film and the second sheet guide faces the second exterior side of the moving film;

(d) proving a detector, which is positioned in the first scanner head, to receive (i) first terahertz radiation that is reflected from the interior surface of the layer of transparent material, (ii) second terahertz radiation that is reflected from the first exterior (top) side of the film, (iii) third terahertz radiation that is reflected from the second interior surface of the film, and (iv) fourth terahertz radiation that is reflected from the reflective surface, wherein the detector is configured to output measurement data corresponding to detection of the first, second, third and fourth terahertz radiation; and (e) calculating (i) the caliper of the moving film independent of the refractive index of the film based on arrival times of the first, second, third and fourth terahertz radiation and/or (ii) the basis weight of the moving the film based on arrival times of the first, second, third and fourth terahertz radiation.

20. The method of claim 19 wherein the source of terahertz radiation generates terahertz radiation having a frequency in the range of 300 GHz to or greater than 4 THz.

\* \* \* \* \*